United States Patent
Shirley et al.

[11] Patent Number: 5,599,288
[45] Date of Patent: Feb. 4, 1997

[54] EXTERNAL LIGAMENT SYSTEM

[75] Inventors: Terry L. Shirley; Thomas R. Shirley, both of Laguna Hills, Calif.

[73] Assignee: GSA, Inc., Laguna Hills, Calif.

[21] Appl. No.: 346,770

[22] Filed: Nov. 30, 1994

[51] Int. Cl.$^6$ .................................................. A61F 5/00
[52] U.S. Cl. ................................................ 602/26; 602/16
[58] Field of Search ............................... 602/16, 20, 23, 602/26, 27; 482/124

[56] References Cited

U.S. PATENT DOCUMENTS

| | | | |
|---|---|---|---|
| 3,804,084 | 4/1974 | Lehman | 602/26 |
| 4,697,583 | 10/1987 | Mason et al. | 602/26 |
| 4,791,916 | 12/1988 | Palz | 602/16 X |
| 4,887,590 | 12/1989 | Loque et al. | 602/26 |
| 4,941,462 | 7/1990 | Lindberg | 602/26 X |
| 4,986,263 | 1/1991 | Dickerson et al. | 602/26 |
| 4,986,264 | 1/1991 | Miller | 602/26 X |
| 5,002,045 | 3/1991 | Spademan | 602/26 X |
| 5,167,612 | 1/1992 | Bonuth | 602/16 X |

OTHER PUBLICATIONS

Donjay Products Catalog "ACL/PCL Support", 1994, p. 50.

*Primary Examiner*—Richard J. Apley
*Assistant Examiner*—Kim M. Lee
*Attorney, Agent, or Firm*—Harry G. Weissenberger, Inc.

[57] ABSTRACT

An external ligament system is formed as part of a flexible knee brace by disposing a pair of cables so that they each run from an anchor point on one side of the leg at the thigh diagonally down across the front of the thigh, around the opposite side of the patella, and down across the front of the calf to an anchor point on the first-mentioned side of the leg at the calf. Rigid linkages hinged at the knee are provided on each side of the leg. The tension of the cable can be varied by pulling the ends of the cables together and securing them with adjustable fasteners.

8 Claims, 5 Drawing Sheets

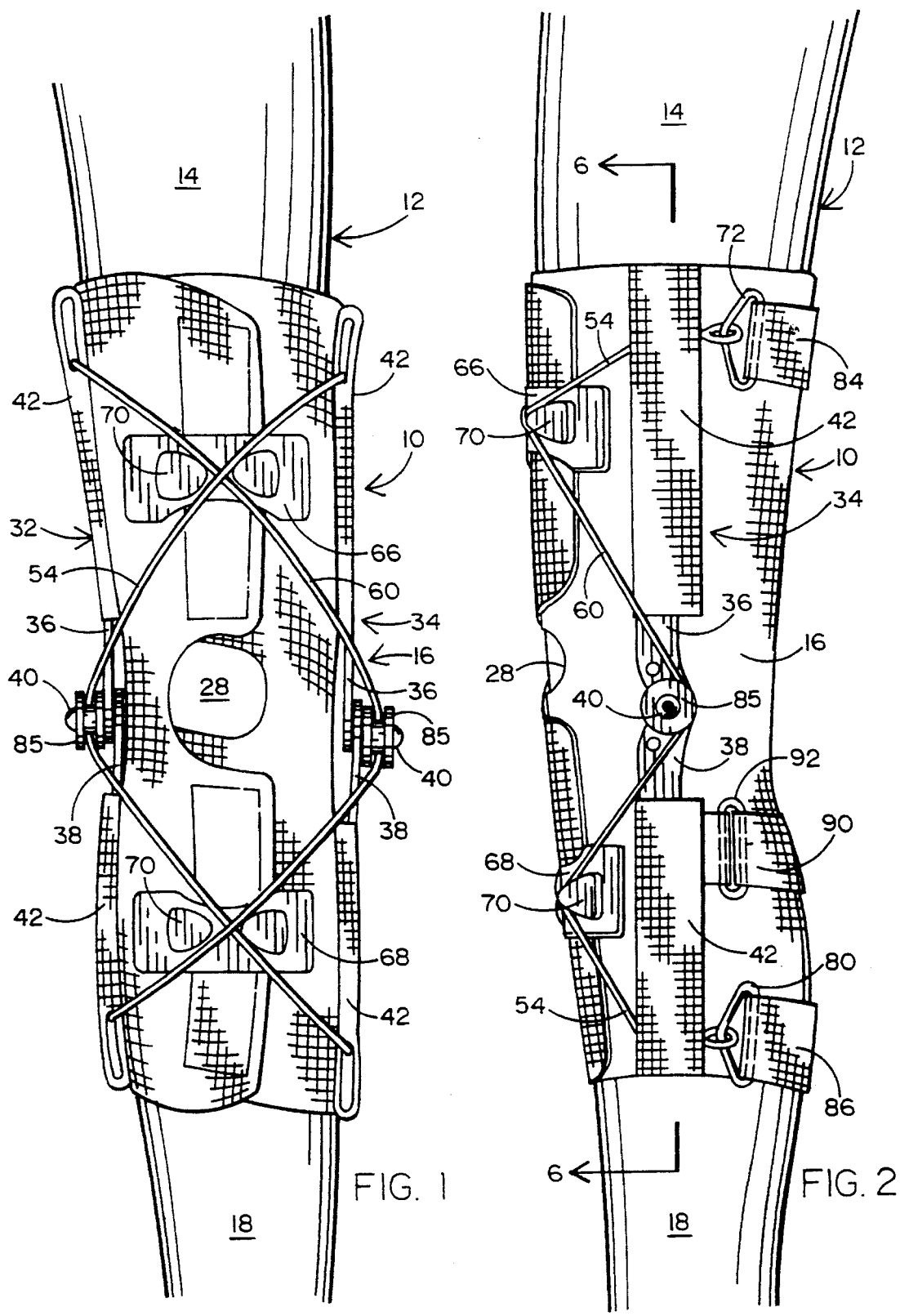

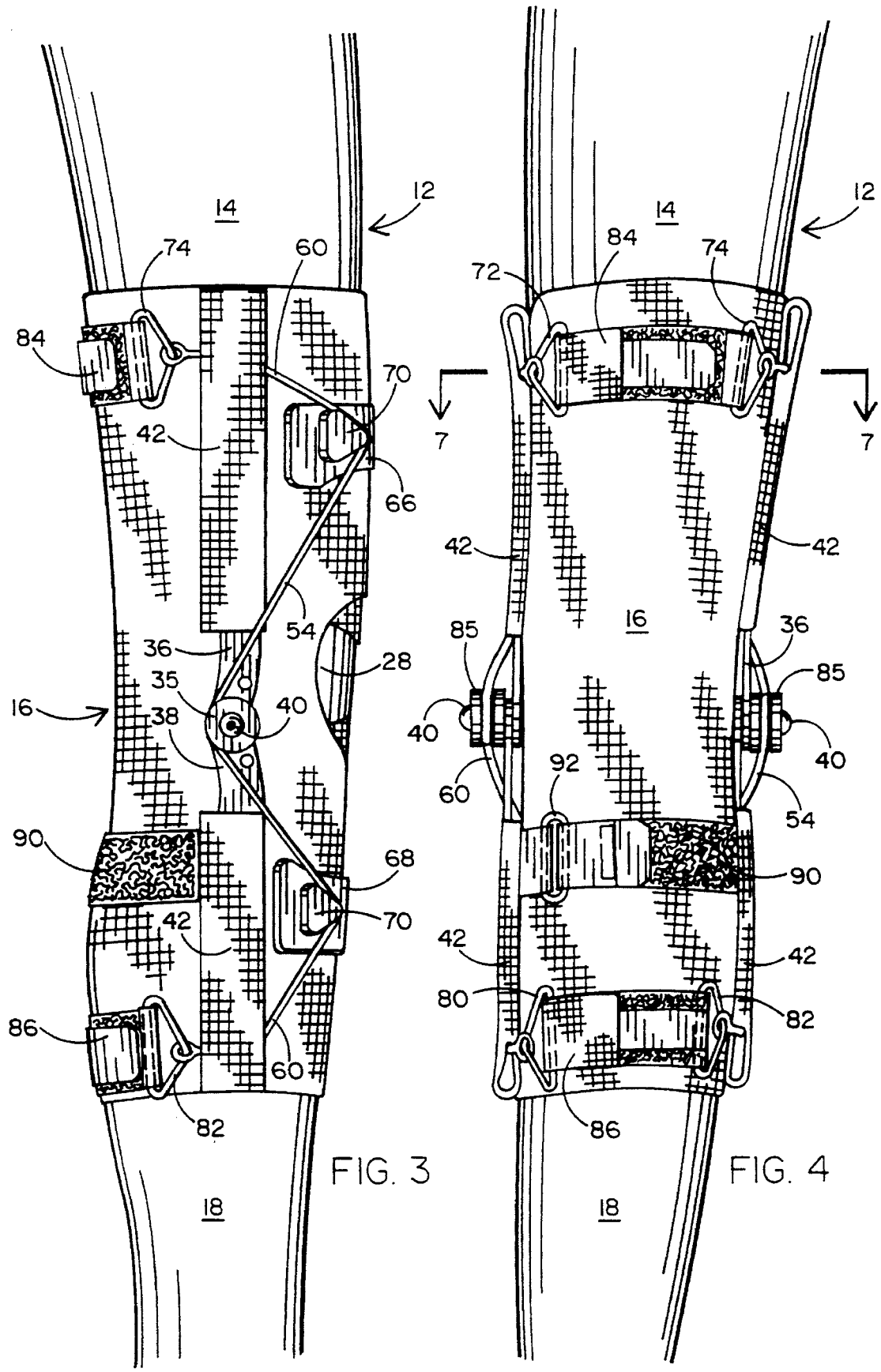

5,599,288

EXTERNAL LIGAMENT SYSTEM

FIELD OF THE INVENTION

This invention relates to knee braces for patients with ligament damage, and more particularly to a lightweight flexible brace using cables as the bracing elements.

BACKGROUND OF THE INVENTION

The mobility and exercise ability of persons who have suffered damage to the ligaments of the knee can be substantially improved by knee braces which hold the tibia and fibula on one hand, and the femur on the other hand, against relative front-to-back motion while allowing the knee to bend.

Conventional knee braces have a rigid frame which includes a rigid femoral cuff attached to the front and sides of the thigh, and a rigid tibial cuff attached to the front and sides of the calf. The femoral cuff and tibial cuff are connected by a rigid, hinged linkage system on each side of the knee whose pivot axis coincides with the center of condyle, i.e. the axis about which the tibia pivots with respect to the femur when the knee is flexed in normal motion.

The above-described conventional braces have three disadvantages: they are relatively heavy; they are expensive; they have to be custom-fitted; and they are awkward to carry or store. Also, when some of the ligaments are still functional, the rigid support provided by conventional braces is not absolutely necessary. In that situation, another conventional knee support is a chloroprene stocking which is flexible but sufficiently firm to maintain the alignment of the femur and tibia against minor stresses. The neoprene stocking has the advantage of being inexpensive and lighter, cooler and more breathable than the rigid braces, but its applicability is limited, particularly if the patient engages in sports or other stressful activity.

A need consequently exists for an inexpensive, off-the-shelf knee bracing system which combines the strength of the rigid braces with the advantages of the chloroprene stocking for patients who need substantial bracing but still have some ligament functionality.

SUMMARY OF THE INVENTION

The invention fulfills the above-described need for a lightweight, inexpensive, off-the-shelf, breathable and highly flexible yet strong knee support by providing an external system in which cables encompassing the knee act much like artificial ligaments in stabilizing the knee joint. The only rigid parts of the inventive system are a pair of flat, hinged linkages on the side of the leg. The remainder of the system (other than the cables and cable fittings) is constructed of sheet-like flexible material which allows the entire system to be folded into a small, lightweight package, and to be adjusted to fit a wide range of users.

The cross-over pattern of the cables in the system of this invention provides stabilization to the patellar region of the knee without the use of a patella cup for high-impact activities.

BRIEF DESCRIPTION OF THE DRAWINGS

FIG. 1 is a front elevation of the system of this invention in place on a user's leg;

FIG. 2 is a left side elevation of the system of FIG. 1;

FIG. 3 is a right side elevation of the system of FIG. 1;

FIG. 4 is a rear elevation of the system of FIG. 1;

DESCRIPTION OF THE PREFERRED EMBODIMENT

Figure 5:
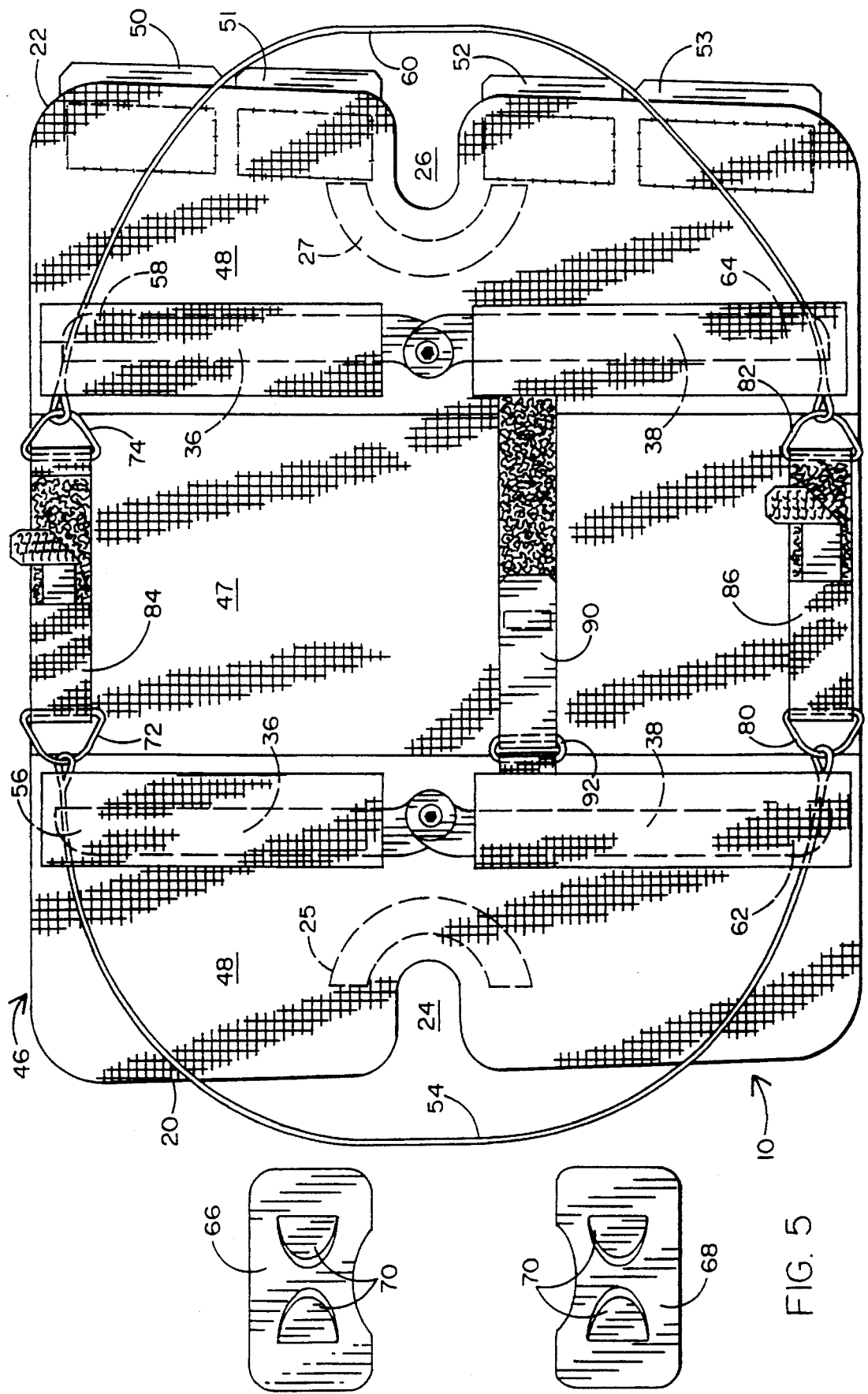
FIG. 5 is a plan view of the system of this invention when spread out flat.

As best shown in FIG. 1, the system of this invention includes an elongated leg sheath 10 which can be wrapped around the leg 12 to extend from the femoral area 14 across the knee 16 to the tibial area 18. The longitudinal sides 20, 22 (FIG. 5) of the sheath 10 are recessed at 24, 26 to leave the patella 28 exposed in order to prevent the sheath 10 from being longitudinally stressed (and thereby applying pressure to the patella 28) when the knee 16 is bent. Cloth-covered foam pads 25, 27 may be provided on the underside of sheath 10 adjacent the recesses 24, 26 to provide padding adjacent the patella for increased comfort.

Figure 6:
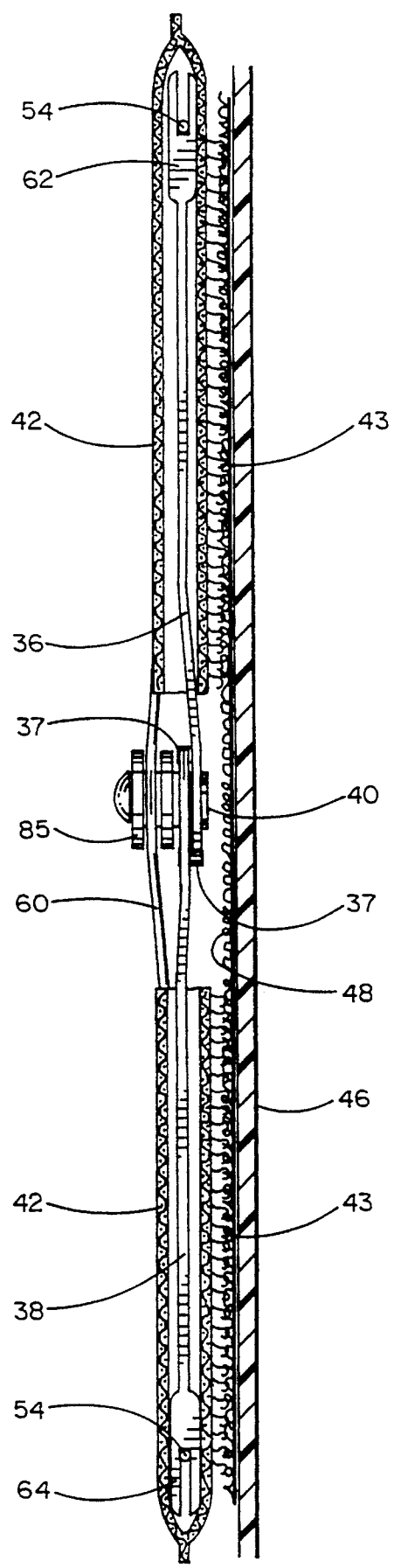
FIG. 6 is a section of a linkage used in this invention, taken along line 6—6 of FIG. 2.
Figure 8:
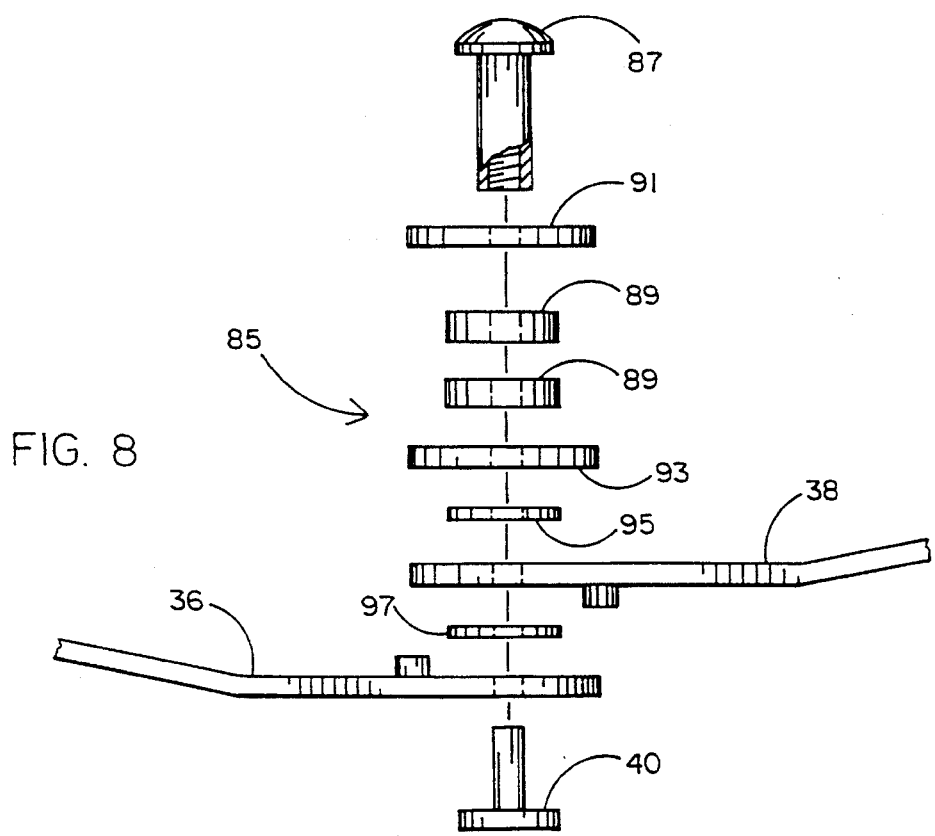
FIG. 8 is an exploded view of the hinge structure of the linkage in this invention.

A pair of hinged linkages 32, 34 are affixed to the sheath 10 in positions where the linkages 32, 34 will be on opposite lateral sides of the knee 16 when the sheath 10 is applied to the leg 12. Each linkage preferably includes a pair of elongated flat plates 36, 38 which are made of steel or other appropriately rigid material and which are pivotably connected to each other by a hinge 40 (FIG. 6). The plates 36, 38 are equipped with stops 37 to prevent the linkages 32, 34 from being pivoted forward past a straight alignment. The plates 36, 38 are preferably encased in protective covers 42 to prevent injury and to facilitate their attachment to the sheath 10 as hereinafter described. In order to accommodate the varying location of the center of condyle in individual patients, the inner side of the cover 42 is provided with Velcro hooks 43 which allow the covers 42, and thereby the plates 36, 38, to be positioned in various positions on the surface of the sheath 10. As best shown in FIGS. 6 and 8, the plates 36, 38 may be equipped at their ends with cable guides 56, 68 and 62, 64 for a purpose hereinafter discussed.

The sheath 10 is preferably formed as a sheet of a firm but flexible rubber-like plastic 46 such as 1–2 mm thick or neoprene (FIG. 7) covered in its central portion with cloth 47, and in its laterally outer portions with a soft loop-surfaced covering 48 for improved breathing of the sheath material such as Lycra or similar material. Hook strips 50, 51, 52, 53 of a Velcro fastening system are applied, respectively, to the underside of the sheet 46 along its side edge 22 for fastening cooperation with the area 48 of the sheet along its side edge 20 when the sheath 10 is wrapped around the leg 12 (FIG. 5).

In accordance with the invention, cables 54, 60 (which may preferably be made of 2.3 mm plastic-coated stainless steel or other material of similar tensile strength such as, e.g. monofilament line) extend through cable guides 56–68, respectively, which are attached to the ends of plates 36 in the femoral area 14, and through cable guides 62, 64, respectively, which are attached to the ends of plates 38 in the tibial area 18. As best shown in FIG. 5, the cables 54, 60 are attached to tensioning loops 72, 74 in the femoral area, and to tensioning loops 80, 82 in the tibial area.

The cables 54, 60 are maintained in the proper crossover alignment by a pair of cable cross guides 66, 68 equipped with Velcro hook strips 69 on their back side, and positioned in use on the front of the sheath 10 above and below the knee 16, respectively. The protuberances 70 on the cross guide 66, 68 maintain the cables 54, 60 in proper crossover alignment with respect to each other as the knee 16 is flexed. The cross guides 66, 68 also distribute the cable load over a larger area of the leg 16.

The tensioning loops 72, 74 and 80, 82 are preferably vinyl-coated triangular bails which can be pulled toward each other by Velcro-equipped tensioning straps 84, 86. The cables 54, 60 are retained on the sheath 10 by the bails 72, 74, 80 and 82 which are too large to pass through the cable guides 56, 58, 62 and 64.

In operation, the sheath 10 of the inventive system is wrapped around the user's leg 12 and is fastened by overlapping the Velcro-equipped side edges of the sheath 10 at the front of the leg 10 so that the recesses 24, 26 leave the patella 28 exposed. The cables 54, 60 are threaded over the grooved rollers 85 at the flexure axis of the knee 16 to form a cross-over helical pattern best illustrated in FIG. 1. The rollers 85, which are attached to the hinges 40, allow the cables 54, 60 to freely follow flexing and twisting movement of the knee 16. The rollers 85 preferably consist of a rivet 87 threaded onto the hinge 40. A pair of O-rings 89 made of rubber or the like are sandwiched between washers 91, 93 to form a deep groove for the cables 54, 60. Washers 95, 97 are provided for improved relative movement of the roller 85 and hinged plates 36, 38. The plastic coating of cables 54, 60 allows them to freely slide over the O-rings 89.

When the cables 54, 60 are pulled as tight as possible by appropriately positioning and attaching the tensioning straps 84, 86, the cables 54, 60 form in essence an external ligament system which reinforces the action of the natural ligaments and prevents the user's upper and lower leg from moving relative to each other in a front-to-rear direction when the knee 16 is exercised.

Figure 7:
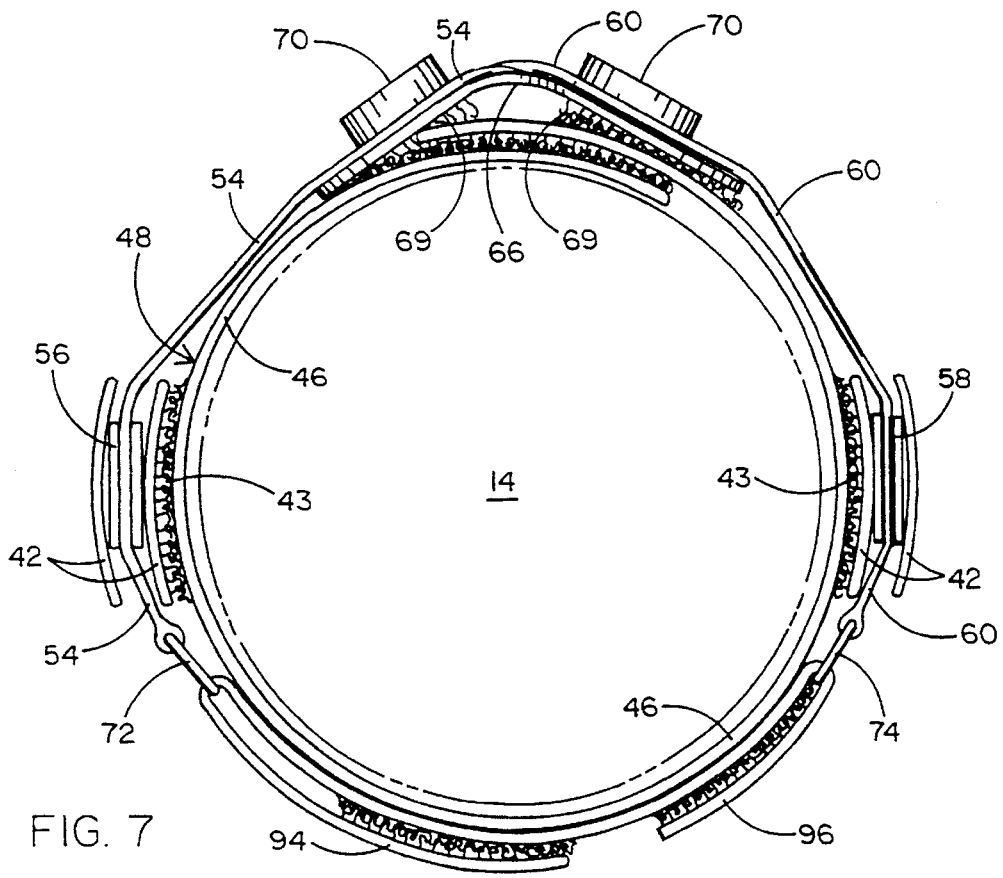
FIG. 7 is a section along line 7—7 of FIG. 4.

A retaining strap 90 is fastened to the sheath 10 just above the calf. The strap 90 can be pulled through a loop 92 attached to the sheath 10 and fastened by overlapping Velcro loop and hook strips 94, 96 (FIG. 7). When tightly fastened, the strap 90 secures the sheath 10 just below the knee and prevents the downward migration of the sheath 10 during use. Also, the strap 90 maintains cable tension by preventing forward movement of the hinges 40 upon flexure of the knee 16.

To use the brace of this invention, the sheath 10 is placed behind the knee 16 with the leg straight, and is tightly wrapped around the leg 12 with the felt side out. The topmost Velcro hook strip 50 is first fastened by pressing it against the felt surface of the sheath 10. The sheath 10 is then aligned on the leg 12, and the remaining hook strips 51, 52, 53 are fastened to the felt surface in positions which ensure that the sheath 10 is tightly wrapped around the leg 12.

Next, the linkages 32, 34 are properly positioned so that the hinges 40 are aligned with each other and with the flexure axis of the knee 16. The linkages 32, 34 are then fixed to the sheath 10 by pressing the Velcro hook strips 43 of the protective linkage covers 42 against the felt surface of sheath 10. The retaining strap 90 is now threaded through the loop 92, pulled tight and fastened by overlapping its Velcro loop and hook strips 94, 96.

The cables 54, 60 are next crossed over each other and are threaded over the rollers 85. The bails 80, 82 are now loosely connected together by tensioning strap 86 which is secured by pressing its Velcro loop and hook strips together. Likewise, the bails 72, 74 are then loosely connected together by tensioning strap 84.

Finally, the cross-guides 66, 68 are inserted under the cable crossovers, and the tensioning straps 84, 86 are tightened to the desired cable tension.

The system of this invention is not meant for patients with serious injuries such as badly torn or cut ligaments. Rather it is meant to enhance the function of lax or partially torn ligaments. Control of the anterior cruciate ligament (ACL) is provided by the lower tensioning strap 84 and helical arrangement of the cables 54, 60 over the femoral area. Posterior cruciate ligament (PCL) control is exercised by the upper and lower tensioning straps 84, 86 as well as the helically positioned cables 54, 60. When the leg 10 is bent, the thigh muscles tend to expand the diameter of the thigh in the region of the upper tensioning strap 84. This action causes the cables 54, 60 to tighten their hold on the lower leg and prevent its front-to-rear movement with respect to the upper leg. In addition, the medial colateral and lateral ligaments of the knee tend to be stabilized by the hinges 40 and plates 36, 38 in the lateral medial area of the knee.

We claim:

1. A knee brace, comprising:
    a) a sheet of flexible material having, in its longitudinal direction, a femoral portion, a knee portion, and a tibial portion;
    b) fastening means arranged to secure the sides of said sheet together when said sheet is wrapped around a user's leg to form a sheath with said sheet's femoral, knee, and tibial portions surrounding, respectively, the femoral area, the knee, and the tibial area of said leg;
    c) cable means arranged to extend, respectively, from a first side of said leg in said femoral portion to the other side of said leg in said knee portion and back to said first side of said leg in said tibial portion, and from said other side of said leg in said femoral portion to said first side of said leg in said knee portion and back to said other side of said leg in said tibial portion; and
    d) tensioning means for tensioning said cable means.

2. The brace of claim 1, further comprising:
    e) substantially rigid linkage means attached to said sheet and extending substantially longitudinally thereof in a position where, when said sheet is wrapped around said leg, said linkage means will be on opposite sides of said knee, said linkage means being hinged in said knee portion.

3. The brace of claim 2, in which said linkage means are movably attached to said sheet, and in which said brace further comprises:
    f) an adjustable strap interconnecting said linkage means in the rear of said leg below said knee but above the calf of said leg.

4. The knee brace of claim 2, in which said linkage means include cable guides substantially adjacent their extremities, said cable guides being so configured that said cable means can slide substantially freely therethrough in the direction longitudinal of said cable means but have limited vertical mobility at said linkage means.

5. The knee brace of claim 1, in which the sides of said sheet are recessed in the knee portion so as to leave the patella uncovered when said sheet is wrapped around said leg.

6. An external ligament system for bracing a leg having a femoral area, a patellar area and a tibial area, comprising
    a) cables extending, respectively, from points on opposing sides of said femoral area, across each other at the front of said leg and around said patellar area via points on the respectively opposite side thereof, and continuing across each other at the front of said leg to points on opposing sides of said tibial area;

b) retaining means on each side of said patellar area for impeding lateral movement of said cables at the sides of said patellar area:

c) tensioning means for tensioning said cables; and d) means for securing said tensioning means to said leg and for securing said cables to said leg at said points.

7. The brace of claim 1, further comprising a plurality of cross guide means positioned on said sheet to maintain said cables in proper crossover alignment when the knee is flexed.

8. The brace of claim 7, in which said cross guide means are releasably attachable to said sheet.

* * * * *